United States Patent
Masciotti et al.

(10) Patent No.: US 11,950,903 B2
(45) Date of Patent: Apr. 9, 2024

(54) REPORTING OF GLYCEMIC VARIABILITY FROM CONTINUOUS GLUCOSE MONITORING

(71) Applicant: Senseonics, Incorporated, Germantown, MD (US)

(72) Inventors: James Masciotti, Germantown, MD (US); Barbara Montgomery, Gaithersburg, MD (US)

(73) Assignee: Senseonics, Incorporated, Germantown, MD (US)

( * ) Notice: Subject to any disclaimer, the term of this patent is extended or adjusted under 35 U.S.C. 154(b) by 497 days.

(21) Appl. No.: 16/191,913

(22) Filed: Nov. 15, 2018

(65) Prior Publication Data

US 2019/0142314 A1    May 16, 2019

Related U.S. Application Data

(60) Provisional application No. 62/586,376, filed on Nov. 15, 2017.

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0004* (2013.01); *A61B 5/7435* (2013.01);
(Continued)

(58) Field of Classification Search
CPC . A61B 5/14532; A61B 5/0004; A61B 5/7435; A61B 5/4842; A61B 5/6801;
(Continued)

(56) References Cited

U.S. PATENT DOCUMENTS 5,341,805 A * 8/1994 Stavridi ............. G01N 21/6486
   600/316
9,795,328 B2   10/2017 Taub et al.
(Continued)

OTHER PUBLICATIONS

Fletcher, Lauren, et al. "Feasibility of an implanted, closed-loop, blood-glucose control device." Immunology 230. (Year: 2001).*
(Continued)

*Primary Examiner* — Kaylee R Wilson
*Assistant Examiner* — Jairo H Portillo
(74) *Attorney, Agent, or Firm* — Rothwell, Figg, Ernst & Manbeck, P.C.

(57) ABSTRACT

In one aspect, a method of estimating an HbA1c level is provided. The method may include obtaining a first and second glucose measurement, adding the first and the second glucose measurements to a glucose measurement data set, and calculating an estimated HbA1c level using at least the glucose measurement data set. In another aspect, a method of calculating a range of an estimated $HbA_{1c}$ level is provided. The method may comprise at least calculating an estimated $HbA_{1c}$ level and a standard deviation of the estimated $HbA_{1c}$ level using a glucose measurement data set, and combining the estimated $HbA_{1c}$ level with the standard deviation of the estimated $HbA_{1c}$ level to acquire the range of the estimated $HbA_{1c}$ level. In another aspect, a glucose monitoring device may display glycemic variability of an individual.

21 Claims, 8 Drawing Sheets

(51) Int. Cl.
*G16H 50/30* (2018.01)
*G16H 10/40* (2018.01)

(52) U.S. Cl.
CPC ............ *G16H 50/30* (2018.01); *A61B 5/4842* (2013.01); *A61B 5/6801* (2013.01); *A61B 5/743* (2013.01); *A61B 5/746* (2013.01); *A61B 5/7465* (2013.01); *G16H 10/40* (2018.01)

(58) Field of Classification Search
CPC ....... A61B 5/743; A61B 5/746; A61B 5/7465; G16H 40/30; G16H 10/40
See application file for complete search history.

(56) References Cited

U.S. PATENT DOCUMENTS

| | | | |
|---|---|---|---|
| 2006/0078908 A1* | 4/2006 | Pitner | G01N 33/54366 435/7.1 |
| 2010/0145174 A1 | 6/2010 | Alferness et al. | |
| 2010/0330598 A1 | 12/2010 | Thukral et al. | |
| 2012/0253840 A1 | 10/2012 | Murata | |
| 2014/0170765 A1* | 6/2014 | Ockenfuss | G01J 3/0256 436/501 |
| 2017/0076630 A1* | 3/2017 | Angelides | A61B 5/4833 |

OTHER PUBLICATIONS

Malka, Roy et al., "Mechanistic Modeling of Hemoglobin Glycation and Red Blood Cell Kinetics Enables Personalized Diabetes Monitoring," Sci Transl Med., 8(359):359ra130, 23 pages (2016).
Temsch, Wilhelm et al., "HbA1c values calculated from blood glucose levels using truncated Fourier series and implementation in standard SQL database language," Methods Inf Med, 47(4): 346-55 (2008).
Higgins, Paul J. et al., "Kinetic Analysis of the Nonenzymatic Glycosylation of Hemoglobin," J Biol Chem, vol. 256, No. 10, pp. 5204-5208 (1981).
Nathan, David M. et al., "Translating the A1C Assay Into Estimated Average Glucose Values," Diabetes Care, vol. 31, No. 8, pp. 1473-1478 (Aug. 2008).
Tahara, Yasuhiro et al., "Kinetics of HbA1c, Glycated Albumin, and Fructosamine and Analysis of Their Weight Functions Against Preceding Plasma Glucose Level," Diabetes Care, Apr. 1995, vol. 18, No. 4, pp. 440-447.

* cited by examiner

REPORTING OF GLYCEMIC VARIABILITY FROM CONTINUOUS GLUCOSE MONITORING

CROSS-REFERENCE TO RELATED APPLICATION

The present application claims the benefit of priority to U.S. Provisional Application Ser. No. 62/586,376, filed on Nov. 15, 2017, which is incorporated herein by reference in its entirety.

BACKGROUND

Field of Disclosure

This disclosure relates to an analyte monitoring system for generating glycemic variability data based on monitored analyte information and displaying the glycemic variability data in a useful manner.

Discussion of Background

Analyte monitoring systems may be used to monitor analyte levels, such as analyte concentrations. One type of analyte monitoring system is a continuous glucose monitoring (CGM) system. A CGM system measures glucose levels throughout the day and can be very useful in the management of diabetes. Through the use of CGMs, patients have access to their current and historical glucose data.

However, the diabetes community has become accustomed to using blood tests ($HbA_{1C}$) to evaluate risks for diabetes complications. While glucose monitoring devices do not measure $HbA_{1C}$, there is a need to estimate $HbA_{1C}$ from monitored glucose levels, so that glycaemia information can be presented to the patient and/or physician in a more familiar format with established guidelines.

Furthermore, a patient may further benefit from a summary of glycemic variability in a graphical report which contains important metrics, such as estimated $HbA_{1C}$, that are related to diabetes complication risks.

Accordingly, presenting the patient metrics that are impactful when considering risks for diabetes complications are also presented to the patient and/or physician with metrics which may be more impactful when considering risks for diabetes complications.

SUMMARY

Aspects of the present invention relate to an improved method of utilizing monitored glucose levels and presenting glycaemia information in an improved and useful way.

One aspect of the invention may provide a method of estimating an $HbA_{1c}$ level. The method may include obtaining a first glucose measurement. The method may include obtaining a second glucose measurement. The method may include adding the first and the second glucose measurements to a glucose measurement data set. The method may include calculating an estimated $HbA_{1c}$ level using the glucose measurement data set, an association constant $k_2$, and an association constant $k_3$. The association constant $k_2$ may represent a conversion of a pre-$A_{1c}$ to an $HbA_{1c}$, and the association constant $k_3$ may represent a life span of the pre-$A_{1c}$ and the $HbA_{1c}$. The method may include displaying the estimated $HbA_{1c}$ level.

In some embodiments, calculating the estimated $HbA_{1c}$ level may comprise taking a convolution of a first function and a second function. The first function may include the glucose measurement data set, and the second function may include the association constant $k_2$ and the association constant $k_3$. In some embodiments, the first function may further include an association constant $K_{eq}$ that represents an equilibrium constant of glucose. In some embodiments, the second function may further include an association constant $k_1$ and an association constant $k_{-1}$, the association constant $k_1$ may represent a binding constant when a glucose attaches to a hemoglobin to form the pre-$A_{1c}$, and the association constant $k_{-1}$ may represent a dissociation constant when the glucose detaches from the hemoglobin.

In some embodiments, the method may further include: receiving a blood $HbA_{1c}$ measurement and calibrating one or more of the first and second functions using the received blood $HbA_{1c}$ measurement. Calibrating the one or more of the first and second functions may further comprise adjusting one or more of the association constant $k_2$, the association constant $k_3$, the association constant $K_{eq}$, the association constant $k_1$, and the association constant $k_{-1}$.

Another aspect of the invention may provide a method of calculating a range of an estimated $HbA_{1c}$ level. The method may include obtaining a first glucose measurement. The method may include obtaining a second glucose measurement. The method may include adding the first and the second glucose measurements to a glucose measurement data set. The method may include calculating an estimated $HbA_{1c}$ level using the glucose measurement data set. The method may include calculating a standard deviation of the estimated $HbA_{1c}$ level using the glucose measurement data set. The method may include combining the estimated $HbA_{1c}$ level with the standard deviation of the estimated $HbA_{1c}$ level to acquire the range of the estimated $HbA_{1c}$ level. The method may include displaying the range of the estimated $HbA_{1c}$ level.

Another aspect of the invention may provide a method by a glucose monitoring device of displaying glycemic variability of an individual. The method may include receiving a data set of glucose measurements of the individual. The glucose measurements may be obtained from the individual during a period of time. The method may include determining a sub-range of a plurality of glucose sub-ranges into which the glucose measurement falls for each glucose measurement in the data set of glucose measurements. The method may include calculating a value indicative of an amount of time that glucose of the individual was within the sub-range using the glucose sub-ranges into which the glucose measurements in the data set of glucose measurements were determined to fall for each of the plurality of glucose sub-ranges. The method may include displaying, on a display, a first graphical element comprising the plurality of glucose sub-ranges and the calculated values indicative of the amounts of time the glucose of the individual was within each of the plurality of glucose sub-ranges during the period of time. In some embodiments, the first graphical element may be a curve graph indicating the amount of time the individual spent at each of the at least one or more glucose levels during the period of time. In some embodiments, the value may be the number of glucose measurements within the sub-range. In some embodiments, the value may be a calculation of a cumulative amount of time within the sub-range. In some embodiments, the value may be a percentage of the period of time that the measured glucose was within the sub-range.

In some embodiments, the method by the glucose monitoring device may further include calculating an average glucose level based on the received data set of glucose measurements. The method may include calculating an estimated $HbA_{1c}$ range based on the received data set of glucose measurements. The method may include calculating a standard deviation of blood glucose based on the received data set of glucose measurements. The method may include displaying, on the display, a second graphical element comprising one or more of the average glucose level, the estimated $HbA_{1c}$ range, the standard deviation of blood glucose, and the defined period of time.

In some embodiments, the method by the glucose monitoring device may further include displaying, on the display, a first area under the curve graph corresponding to a first sub-range of the plurality of glucose sub-ranges as a first color. The method may include calculating an area of the first area under the curve graph. The method may include displaying, on the display, a second graphical element comprising the calculated area of the first area under the curve graph.

In some embodiments, the method by the glucose monitoring device may further include displaying, on the display, a second area under the curve graph corresponding to a second sub-range of the plurality of glucose sub-ranges as a second color. The method may include calculating an area of the second area under the curve graph. The method may include and displaying, on the display connected to the glucose monitoring device. The second graphical element may further comprise the calculated area of the second area under the curve graph.

Other features and characteristics of the subject matter of this disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

The accompanying drawings, which are incorporated herein and form part of the specification, illustrate various embodiments of the subject matter of this disclosure. In the drawings, like reference numbers indicate identical or functionally similar elements.

DETAILED DESCRIPTION

Figure 1:
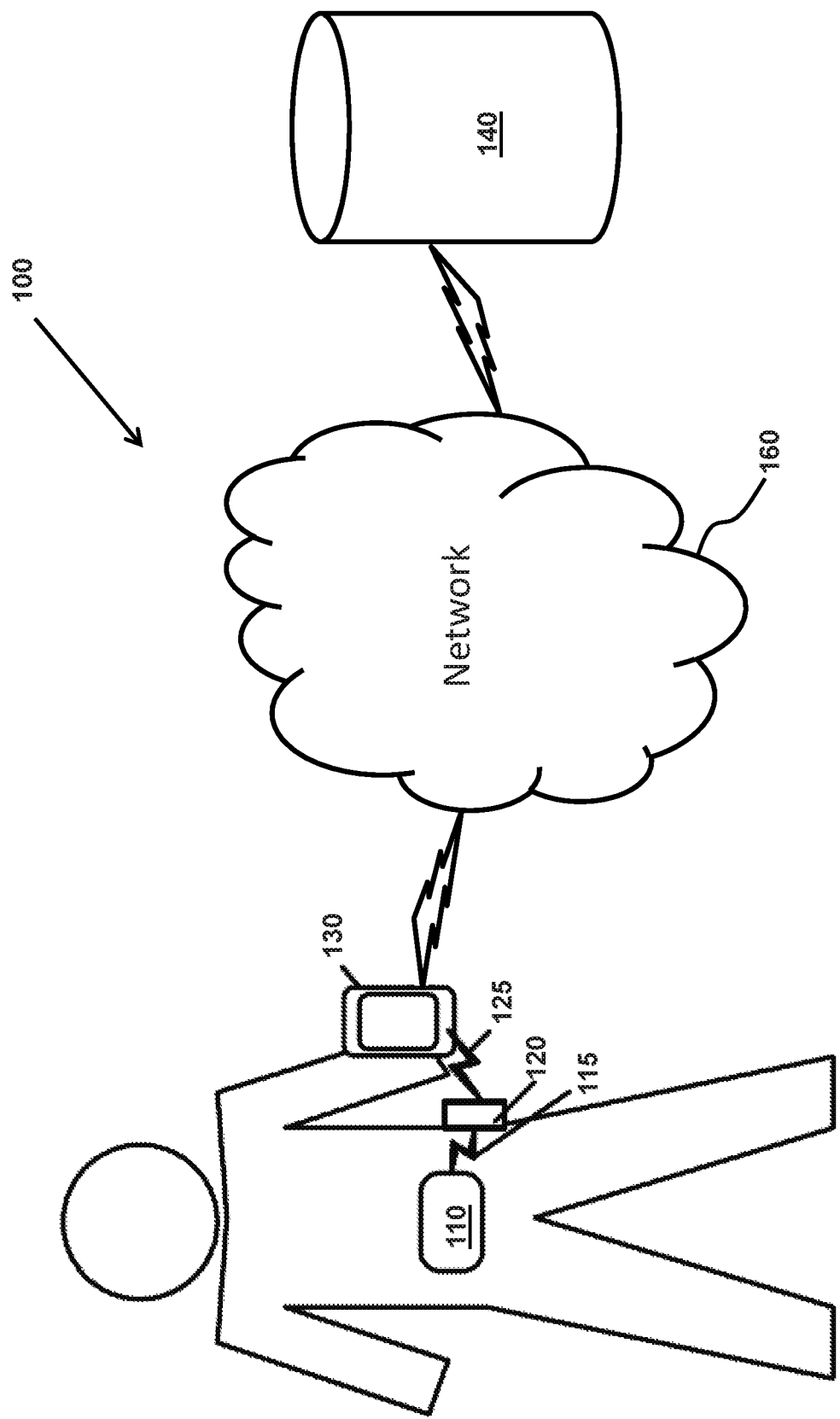
FIG. 1 is a block diagram illustrating an analyte monitoring system embodying aspects of the present invention.

FIG. 1 is a block diagram of an analyte monitoring system 100 illustrating connectivity between a plurality of devices that are configured to obtain sensor-measured analyte information from a wireless analyte monitoring sensor according to one non-limiting embodiment of the present invention. In some embodiments, as shown in FIG. 1, the analyte monitoring system 100 may include one or more of an analyte monitoring sensor 110, a transceiver 120, a primary device 130 and a data management system (DMS) 140. In some embodiments, the primary device 130 and the DMS 140 may be in communication with each other via a network 160. In some embodiments, the analyte monitoring sensor 110 is in communication with the transceiver 120 over a first communication link 115. In some embodiments, the first communication link 115 may be a wireless communication link or a wired communication link. Examples of wired communication links comprise, but are not limited to: cable, wire, twisted-pair wire, fiber-optic, Ethernet, USB, and/or the like. Examples of wireless communications links comprise, but are not limited to: cellular, Wi-Fi, Bluetooth™, Near-Field Communications (NFC), infrared, radar, satellite, radio frequency, combinations thereof, and/or the like. In some embodiments, the transceiver 120 may be in communication with the primary device 130 by a second communication link 125. In one embodiment, the second communication link 125 may be a wireless link, such as Bluetooth™.

In some embodiments, the primary device 130 and the DMS 140 may be in communication with each other via the network 160. In some embodiments, the primary device 130 may be configured to transmit sensor-measured analyte information to the DMS 140. The network 160 may comprise, but is not limited to: local area network (LAN), wide area network (WAN), the Internet, intranets, cellular, combinations thereof, and/or the like.

In some embodiments, the analyte monitoring sensor 110 may be a wireless, implantable sensor inserted subcutaneously inside a patient. In some embodiments, the analyte monitoring sensor 110 may be configured to measure interstitial fluid glucose levels of the patient. In some embodiments, the analyte monitoring sensor 110 may comprise, for example, a fluorometer. A fluorometer or fluorimeter may comprise a device configured to measure parameters of fluorescence such as, for example, its intensity and/or wavelength distribution of emission spectrum after and/or during excitation by a spectrum of light. These parameters may be employed to identify the presence and/or the amount of specific molecules in a medium.

In some embodiments, the analyte monitoring sensor 110 may be configured to communicate the measured analyte information to the transceiver 120 over either a wired communication link or a wireless communication link. In some embodiments, the transceiver 120 may be configured to receive the measured analyte information from the analyte monitoring sensor. In some embodiments, the transceiver 120 may additionally be configured to power the analyte monitoring sensor via wireless power transfer mechanisms. In some non-limiting embodiments, the transceiver 120 may be connected to a power source, such as a battery, a transformer, a power line, or the like. In some embodiments, the transceiver 120 may transmit power by electromagnetic fields across an intervening space to one or more receiver devices. In some embodiments, the analyte monitoring sensor 110 may connect the electromagnetic fields back to electric power and utilize the power. In some embodiments, the transceiver 120 may be a reusable device disposed external to the patient at a location within communications range of analyte monitoring sensor 110. Depending upon the power capabilities of transceiver 120, the location of transceiver 120 may be on or near the skin of patient and/or at a distance from patient. In some embodiments, the transceiver 120 may be configured to communicate to one or more of the devices over one or more communications links. By communicating to one or more devices, the transceiver 120 may be configured to transmit the analyte information obtained from the analyte monitoring sensor 110 to the one or more devices of the analyte monitoring system 100. In an embodiment, the transceiver 120 may be configured to transmit the analyte information obtained from the analyte monitoring sensor 110 to the primary device 130 and/or the DMS 140.

In some embodiments, the primary device 130 of the analyte monitoring system may comprise a mobile display device such as, but not limited to: a smart phone, a tablet, an iPod, a health monitoring watch, and/or the like. However, in some alternative embodiments, the plurality of devices of the analyte monitoring system may comprise another type of display device such as, but not limited to: a personal computer, a netbook, a medical monitoring device, and/or the like. Furthermore, the primary device 130 may comprise a medical device, such as, but not limited to: a blood glucose meter, an insulin pump, a combination thereof, and/or the like. In some embodiments, the primary device 130 may be configured to receive monitored analyte information transmitted by the transceiver 120. The primary device 130 may store the received analyte information in memory for further processing. In some embodiments, the primary device 130 may additionally or alternatively transmit the received analyte information to the DMS 140.

In some embodiments, the DMS 140 may be a server device employed to allow data to be shared over the network such as the Internet. The server may share data via proprietary formats configured to be employed by hardware computing systems configured, at least in part, with applications to make the hardware computing system into an analyte monitoring system. In some embodiments, the DMS 140 may be a web-based DMS (e.g., hosted on a remote server). In some embodiments, monitored analyte information transmitted by the primary device 130 and/or the transceiver 120 may be uploaded (e.g., through a wired connection such as, for example, a USB connection or a wireless connection such as, for example, a wireless Internet connection) to the DMS 140. In some embodiments, the DMS 140 may enable sharing of the analyte data (e.g., allowing the user, caregiver, and/or clinician to view sensor analyte data). The user may collect analyte data at home or in a clinic/research facility and then upload the data to their computer web account. Using the web account, the DMS 140 may use the data to generate one or more different reports utilizing the uploaded information. For example, in some non-limiting embodiments, the DMS 140 may use the uploaded data to generate one or more of the following reports: (i) an analyte details report, (ii) an analyte line report, (iii) a modal day report, (iv) a modal summary report, (v) a statistics report, and (vi) a transceiver log report. In an embodiment the DMS 140 may include one or more storage device(s). Some of the storage devices may comprise a web accessible software as a services storage such as, for example, DropBox™, Google™ Drive, Microsoft™ OneDrive™, Amazon™ S3 storage, combinations thereof, and/or the like.

Figure 2:
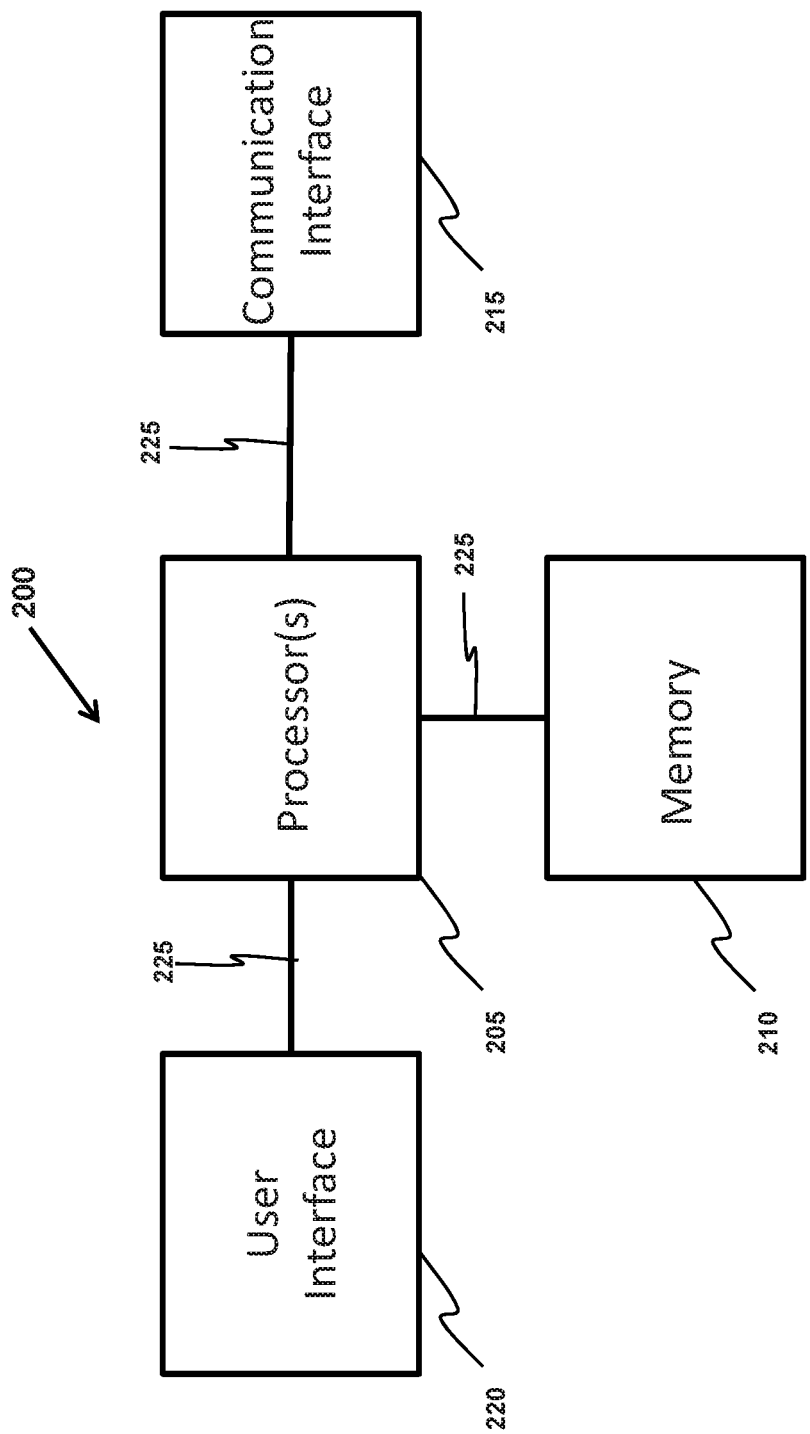
FIG. 2 is a block diagram illustrating a processing system of a device embodying aspects of the present invention.

FIG. 2 illustrates a processing system 200 residing in a device of analyte monitoring system according to an embodiment of the present invention. In some embodiments, shown in FIG. 2, each device of the analyte monitoring system may include a processing system 200 consisting of one or more processors 205, a memory 210, a communication interface 215, a user interface 220, and/or a bus 225 that couples the various processing system components including the memory 210 to the one or more processors 205. In some embodiments, the one or more processors 205 may consist of one or more central processing units (CPUs) that execute computer program instructions stored in the memory 210 to perform functions described herein with respect to the one or more devices. These functions may be configured to improve the technological field of analyte monitoring and drug dispersion on a living patient. In some embodiments, the memory 210 may include computer storage media in the form of volatile and/or nonvolatile memory such as ROM and RAM. In some embodiments, the memory 210 may additionally or alternatively include non-removable nonvolatile computer storage media, such as, for example and without limitation, a hard disk drive or removable nonvolatile computer storage media that is configured to read from a flash drive, optical disk drive, or other optical media. In some embodiments, the drives and their associated computer storage media may provide storage of computer readable instructions, data structures, program modules and other data for the processing system, which are inputted to the one or more processors for the performance of particular tasks.

In some embodiments, the user interface 220 of the processing system 200 may enable an operator to control the device (e.g., primary device 130) by providing one or more input and/or output devices. The input and/or output devices may include, for example and without limitation, pushbutton(s), a keyboard, a microphone, a camera, a pointing device (e.g., a mouse, trackball, or touch pad), touch screen(s), voice interfaces(s), multimedia interface(s), audio interface(s), tactile interfaces(s), visual interface(s), monitor(s), combinations thereof, and/or the like. Accordingly, in some embodiments, a user may enter commands and information into the device through input devices, and the device may present the analyte information to the user via the output devices.

In some embodiments, the communication interface 215 of the processing system 200 may enable the device to be operated in a networked environment using logical connections to the analyte monitor sensor, transceiver, and other devices of the analyte monitoring system. In some embodiments, the communication interface 215 is configured to communicate directly with analyte sensor. In some alternative embodiments, the communication interface 215 may be configured to additionally or alternatively relay analyte information obtained from the analyte sensor to other devices of the analyte monitoring system. Through the communication interface 215, the device may be connected to a remote application program residing on a remote processing device, in which the device and the remote processing device are linked via the network. Accordingly, the device may delegate particular tasks to the remote application program residing on the remote processing device.

Figure 3:
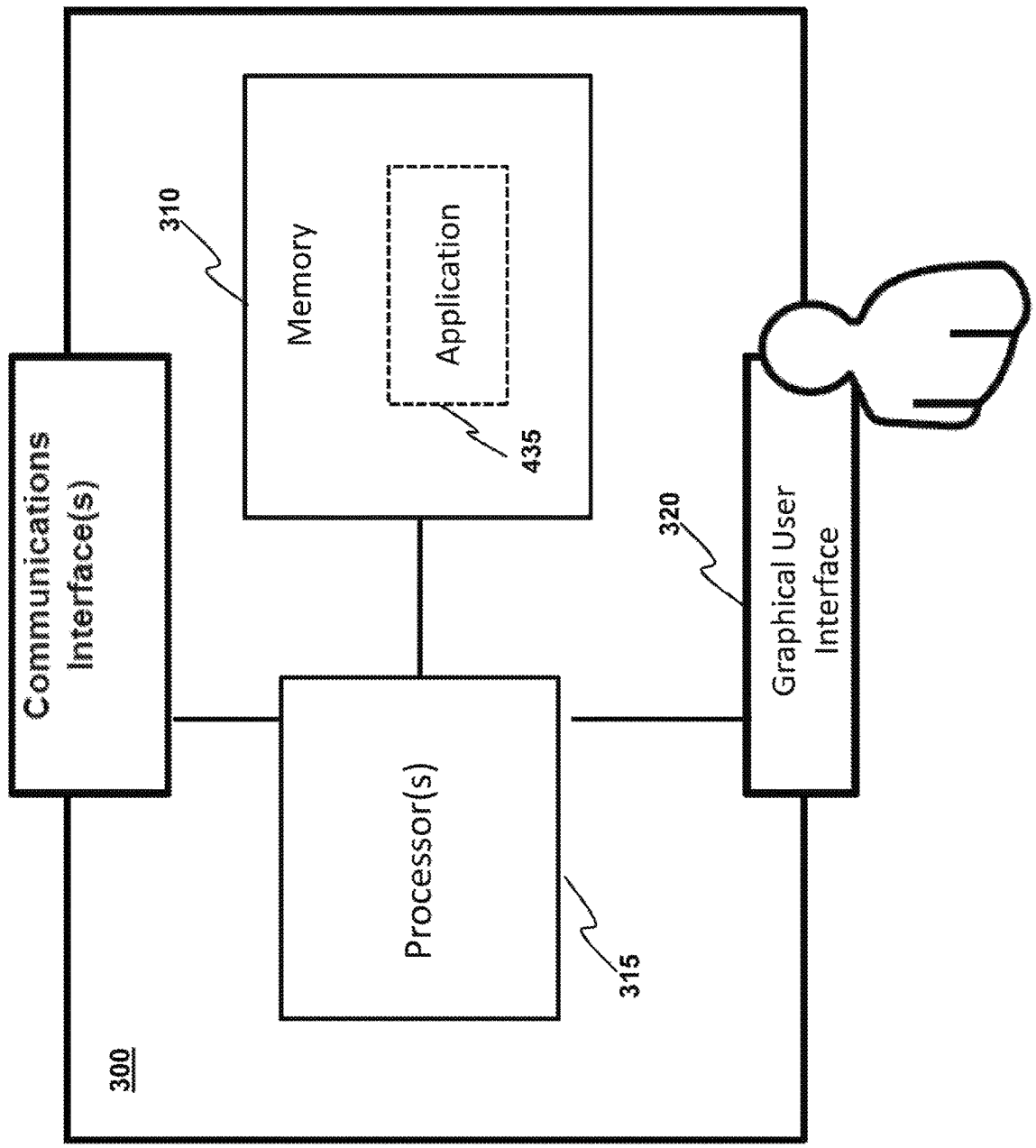
FIG. 3 is a block diagram illustrating a processing system of a device embodying aspects of the present invention.

One or more mobile medical applications 305 ("MMA") may be provided, for example, to execute in the plurality of devices of the analyte monitoring system 100. Referring to FIG. 3, the MMA 305 is provided in the form of computer readable instructions stored in the memory 310 of a device 300 and is configured to be executed by the one or more processors 315 in the processing system of the device 300 according to an embodiment of the present invention. Where the device 300 is coupled to a display 320, the MMA 305 may cause the device 300 to provide a series of graphical control elements or widgets, such as a graphical user interface (GUI), shown on the display 320. As a result, the MMA 305 may, for example, cause the device 300 to display analyte related information in a GUI such as, but not limited to: one or more of glucose information, current glucose readings, user notifications, glucose status alerts and alarms, trend graphs and arrows, and user-entered events, and may provide one or more graphical control elements that may allow a user to manipulate aspects of the one or more display screens. In another embodiment, the MMA 305 may cause the device 300 to display one or more of the reports generated by the DMS 140, such as: (i) the analyte details report, (ii) the analyte line report, (iii) the modal day report, (iv) the modal summary report, (v) the statistics report, and (vi) the transceiver log report. Although aspects of the MMA 305 are described in the context of glucose monitoring system embodiments, this is not required, and, in some alternative embodiments, the MMA 305 may be employed in other types of analyte monitoring systems.

Displaying an Individual's Monitored Glycemic Variability

Figure 4:
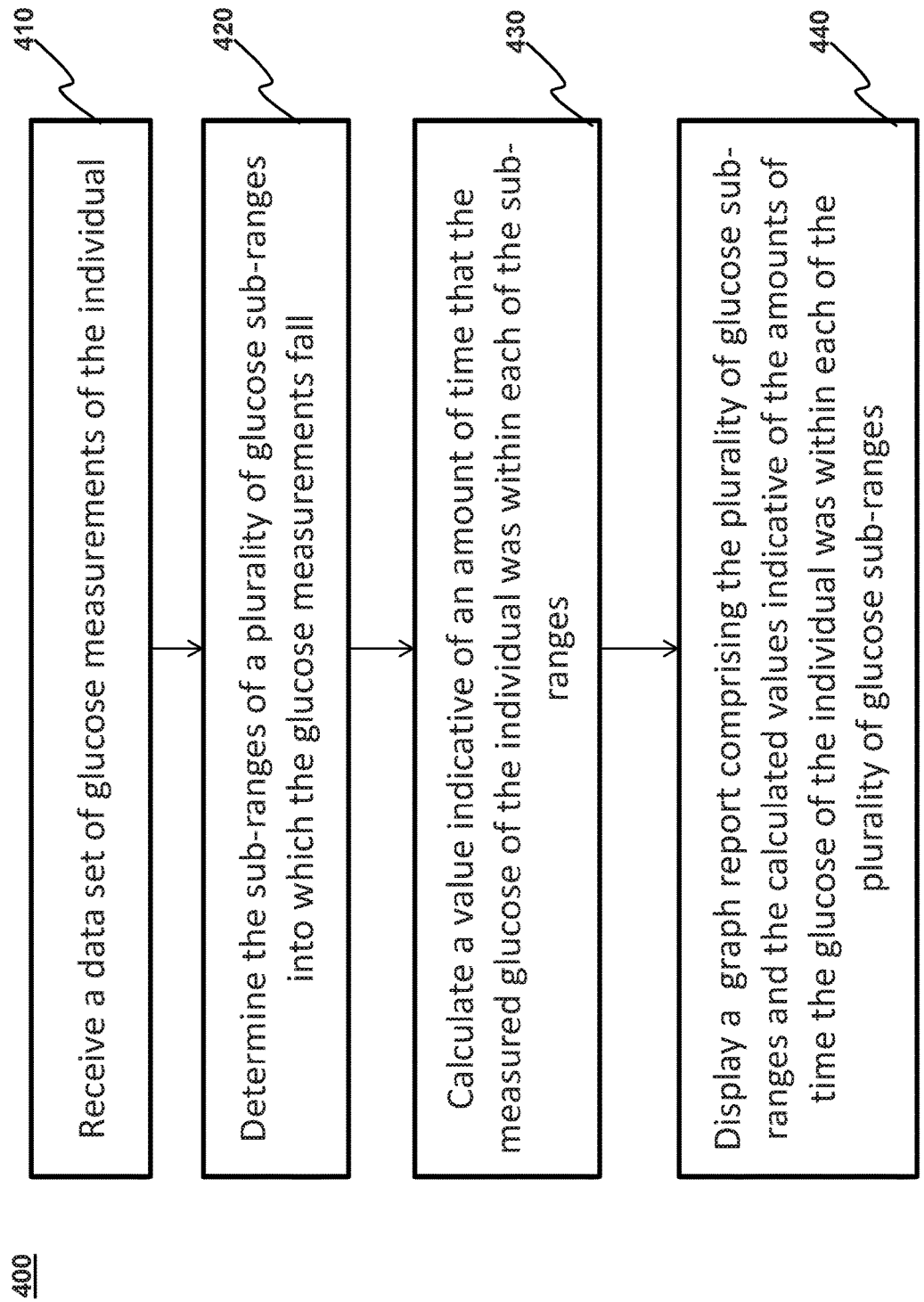
FIG. 4 illustrates a flowchart of a method for generating and displaying an exemplary graphical report regarding an individual's monitored glycemic variability and embodying aspects of the present invention.

FIG. 4 illustrates a flowchart of a method 400 for generating and displaying an exemplary graphical report regarding an individual's monitored glycemic variability, according to an embodiment of the present invention. In some embodiments, one or more steps of the method 400 may be processed by the MMA 305 provided in the primary device 130. However, the method 400 is not restricted to the combination of the MMA 305 and the primary device 130, in some alternative embodiments, and may be processed by any device in the analyte monitoring system 100. In some embodiments, the method 400 may be processed by the DMS 140.

In some embodiments, the method 400 may include a step 410, in which the MMA 305 receives a data set of glucose measurements of the individual. The data set of glucose measurements may be based on the analyte information obtained from the one or more analyte monitoring sensors 110. The received data set of glucose measurements may comprise glucose measurements of the individual obtained over a period of time. In some non-limiting embodiments, the period of time may be, for example and without limitation, the most recent 30 days, and the received data set of glucose measurements may reflect glucose measurements obtained from the individual in that period of time. In some embodiments, the period of time may be any time range in which glucose measurements have been obtained from the individual.

In some embodiments, the method 400 may include a step 420, in which for each glucose measurement in the data set of glucose measurements, the MMA 305 determines the sub-ranges of a plurality of glucose ranges into which the glucose measurement falls. A glucose measurement may typically fall within an expected range (e.g., from 0 to 300 mg/dL). In some embodiments, an expected range may be divided into a plurality of sub-ranges. For example, in some non-limiting embodiments, an expected range may be divided into three sub-ranges. The three sub-ranges may correspond to a hypoglycemic sub-range (e.g., less than 70 mg/dL or less than 80 mg/dL), a target glucose 180 mg/dL or 80 mg/dL to 180 mg/dL), and a hyperglycemic range (e.g., greater than 180 mg/dL). For another example, an expected sub-range may be divided into five sub-ranges (e.g., less than 70 mg/dL, 70-100 mg/dL, 100-160 mg/dL, 160-180 mg/dL, and greater than 180 mg/dL). For still another non limiting embodiment, an expected range may be divided into two sub-ranges. The two sub-ranges may correspond to a target range (e.g., 70-180 mg/dL) and an out-of-target range (e.g., less than 70 mg/dL and greater than 180 mg/dL). For yet another example, an expected range may be divided into 300 sub-ranges, such as 120-120.9 mg/dL, 121-121.9 mg/dL, and so on. An obtained glucose measurement of 120.5 mg/DL would fall within the 120-120.9 mg/dL sub-range. In some embodiments, the number of glucose concentration sub-ranges may vary depending on the processing capabilities and sophistication of the primary device 130.

In some embodiments, the method 400 may include a step 430, in which for each of the plurality of glucose concentration sub-ranges, the MMA 305 calculates a value indicative of a cumulative amount of time that the measured glucose of the individual was within each of the sub-range using the sub-ranges into which the glucose measurements in the data set of glucose measurements were determined to fall. In some non-limiting embodiments, the MMA 305 may calculate the value indicative of the cumulative amount of time within the sub-range by aggregating the number of glucose measurements falling within each of the plurality of glucose concentration sub-ranges. In these embodiments, the value indicative of the cumulative amount of time that the measured glucose of the individual was within the sub-range may be the aggregate number of glucose measurements within the sub-range.

In some non-limiting alternative embodiments, in step 430, the MMA 305 may calculate the value indicative of the cumulative amount of time within the sub-range by, for each sub-range, calculating the cumulative amount of time that the measured glucose of the individual was within the glucose sub-range based on (i) the aggregate number of glucose measurements within that sub-range and (ii) the periodic time interval between glucose measurements (e.g., 1, 2, 5, 10, 15 or 20 minutes). In these embodiments, the value indicative of the cumulative amount of time that the measured glucose of the individual was within the sub-range may be a calculation of the cumulative amount of time within the sub-range (e.g., the aggregate number of glucose measurements within that sub-range multiplied by the periodic time interval between glucose measurements).

In some embodiments, in step 430, the MMA 305 may calculate a percentage of time that the measured glucose was within each sub-range. In some non-limiting embodiments, the MMA 305 may calculate a percentage of time that the measured glucose was within a sub-range by comparing the aggregate number of measurements within a sub-range during a period of time with the total number of measurements obtained during the period of time. In some non-limiting alternative embodiments, the MMA 305 may calculate a percentage of time that the measured glucose was within a sub-range by comparing a cumulative amount of time that the measured glucose of the individual was within the glucose sub-range during a time period with the time period.

In some embodiments, the MMA 305 may calculate an average glucose (AG) level and a standard deviation of blood glucose (SDBG) based on the received data set of glucose measurements. In some embodiments, the MMA 305 may additionally or alternatively calculate an estimated $HbA_{1c}$ range ($eHbA_{1c}$) based on the received data set of glucose measurements, as will be discussed in further detail in FIGS. 6A-B.

Figure 5:
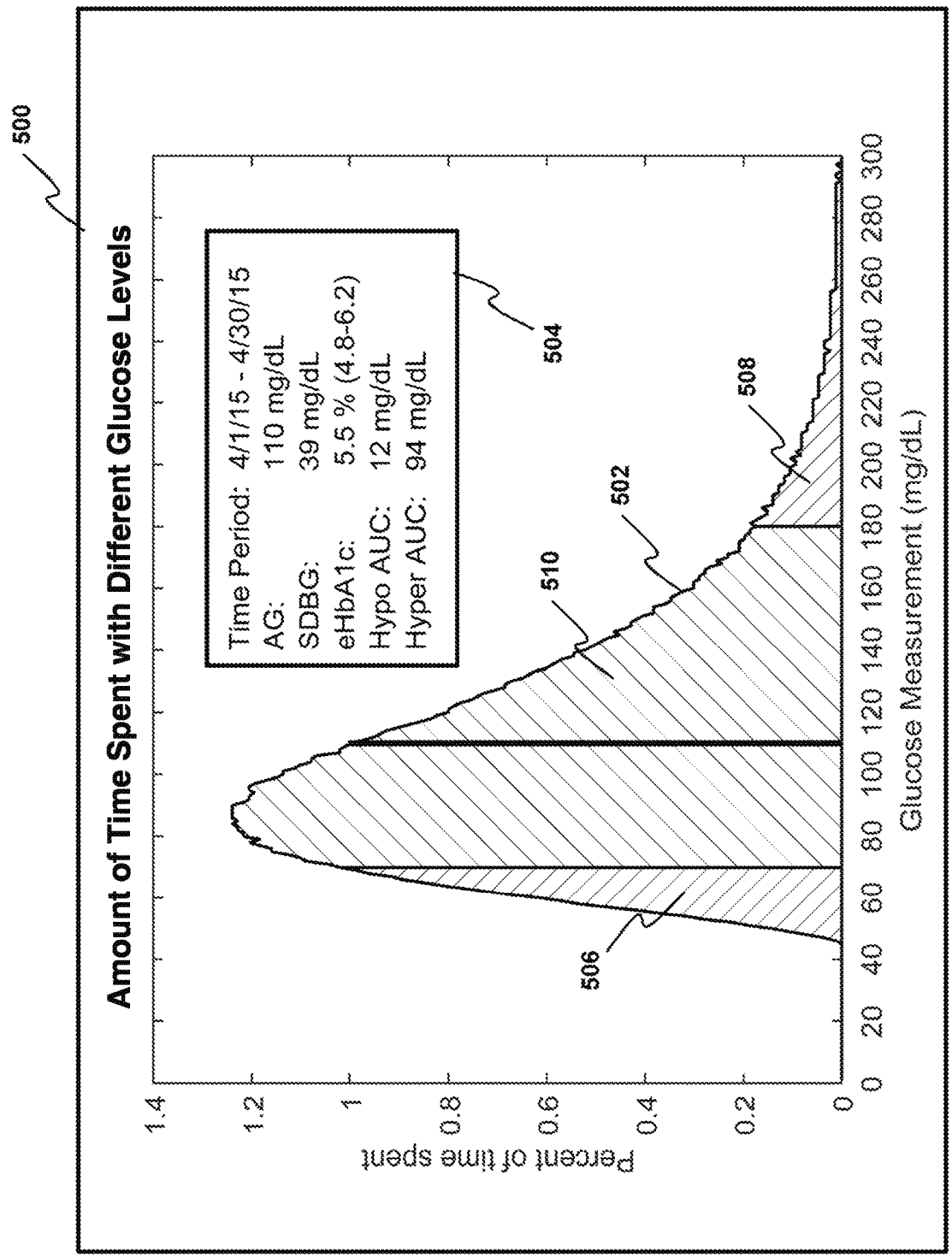
FIG. 5 illustrates an exemplary embodiment of the graph report and embodying aspects of the present invention.

In some embodiments, the method 400 may include a step 440, in which the MMA 305 may cause the primary device 130 to display a graph report comprising one or more of a curve indicating the plurality of glucose ranges and the values indicative of the cumulative amounts of time the glucose of the individual was within each of the plurality of glucose ranges during the period of time. FIG. 5 shows a non-limiting example of a graph report 500 that may be generated and displayed by method 400 in accordance with some embodiments.

In some embodiments, as illustrated in FIG. 5, the graphical report 500 may comprise a curve 502. In some embodiments, the x-axis of the graph may indicate the monitored glucose measurement, and a y-axis of the graph indicates the percentage of time spent at each monitored glucose measurement. Accordingly, the curve graph 502 indicates the amount of time the individual had spent at each of the plurality of glucose ranges during the period of time. The graphical report 500 further comprises a legend 504 containing at least one or more of: (i) the time period indicating when the received data set of glucose measurements were obtained from the individual, (ii) the average glucose (AG) level, (iii) the standard deviation of blood glucose (SDBG), and (iv) the estimated $HbA_{1c}$ range (e$HbA_{1c}$).

In an embodiment, the graphical report 500 contains an indication regarding the amount of time spent by the individual at low and/or high glucose levels. As shown in FIG. 5, the graphical report 500 highlights an area under the curve graph 502 corresponding to a low glucose level, referred to as the Hypo Area Under Curve (Hypo AUC) 506, by displaying the Hypo AUC 506 as a different color compared to the area under the curve graph 502 pertaining to a normal range of glucose levels 510. Similarly, the graphical report 500 highlights an area under the curve graph 502 corresponding to a high glucose level, referred to as the Hyper Area Under Curve (Hyper AUC) 508, by displaying the Hyper AUC 508 as a different color. In an embodiment, the MMA 305 calculates the area of both Hypo AUC 506 and Hyper AUC 508, respectively. The calculated areas of Hypo AUC 506 and Hyper AUC 508 may be included in the legend 504 of the graphical report 500.

Estimating an $HbA_{1c}$ Range Based on Monitored Glucose Measurements

The diabetes community uses blood tests ($HbA_{1c}$) to evaluate risks for diabetes complications. While glucose monitoring devices do not measure $HbA_{1c}$, there is a need to estimate $HbA_{1c}$ from monitored glucose levels, so that glycaemia information can be presented to the patient and/or physician in a more familiar format with established guidelines.

The conventional understanding of the mathematical relationship between $HbA_{1c}$ and average glucose (AG) is defined according to Nathan's formula[1]:

$$AG = a + b \times A1C \pm t_{n-1,1-\alpha/2} \times \sigma_{(AG|A1C)} \quad (1)$$

$$\sigma_{(AG|A1C)} = \sqrt{\left(1 + \frac{1}{n}\right)\beta_1 A1C^{\beta_2}}, \quad (2)$$

where $\sigma_{(AG|A1C)}$ is the standard deviation of AG, $t_{n-1,1-\alpha/2}$ is 1.648, a=46.7, b=28.7, $\beta_1$=4.81, $\beta_2$=2.03.

[1] See Nathan et al., "Translating the A1C Assay Into Estimated Average Glucose Values" Diabetes Care, Vol. 31, No. 8, August, 2008, which is hereby incorporated herein, in its entirety, by reference thereto.

Accordingly, the current universal method of estimating an AG based on $HbA_{1c}$ uses the following simplified version of equation (1):

$$AG = 28.7 \times HbA_{1c}(\%) - 46.7 \quad (3)$$

Taking the inverse of the standard linear AG estimation equation (3) leads to the following equation for estimating an $HbA_{1c}$ level:

$$HbA_{1C}(\%) = \frac{AG + 46.7}{28.7} \quad (4)$$

However, this conventional method of acquiring an estimated $HbA_{1c}$ level may be problematic because the resulting estimated $HbA_{1c}$ level is based on an average glucose level over a period of time. That is, the average glucose level may not reflect how severely the glucose level may have potentially fluctuated throughout the period of time. Accordingly, there is a need for a method of estimating an accurate $HbA_{1c}$ level based on a data set comprising continuously monitored glucose measurements.

Figure 6A:
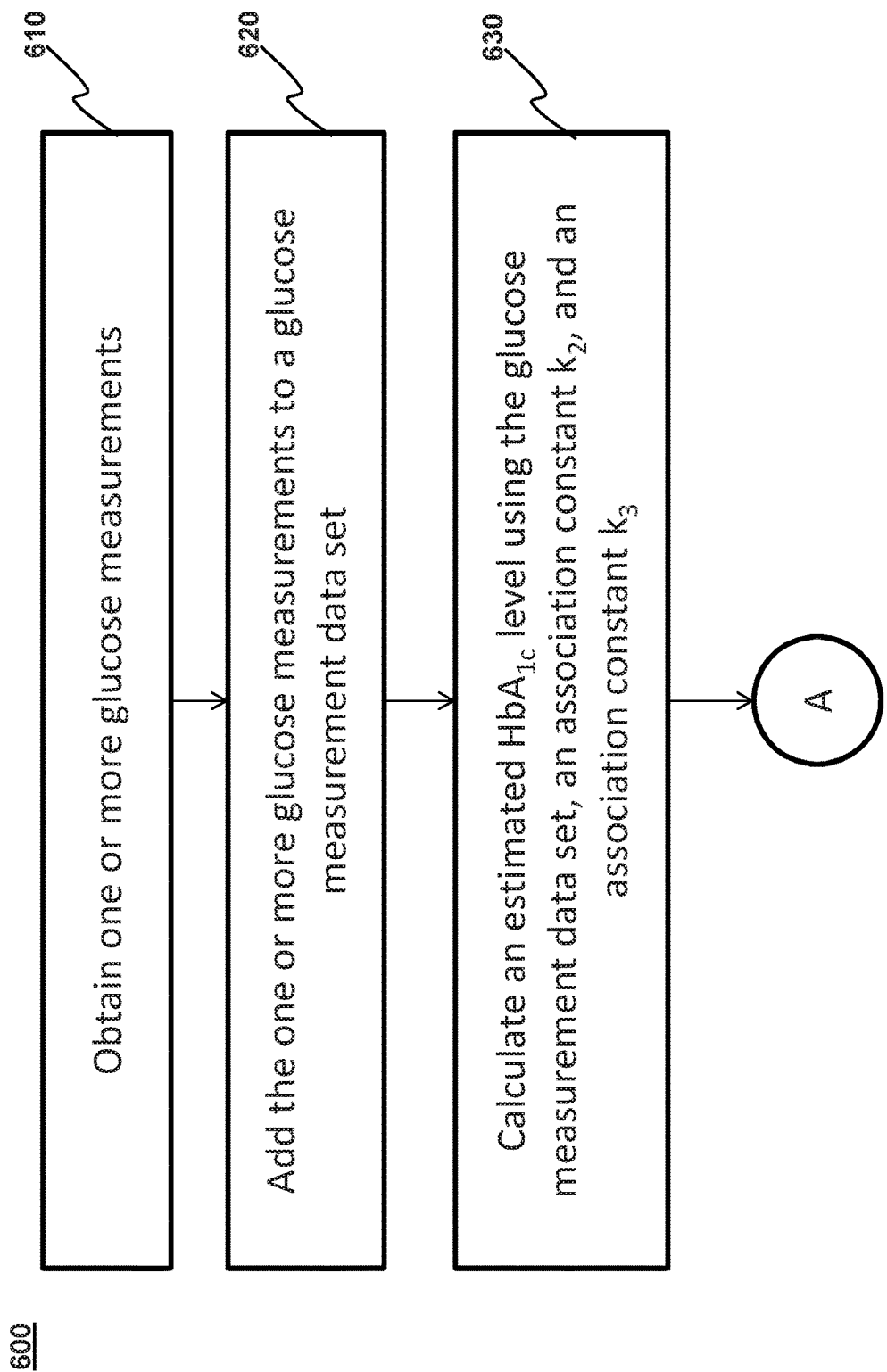
FIGS. 6A-6B illustrate a flowchart of an exemplary method 600 of estimating an $HbA_{1c}$ level and embodying aspects of the present invention.
Figure 6B:
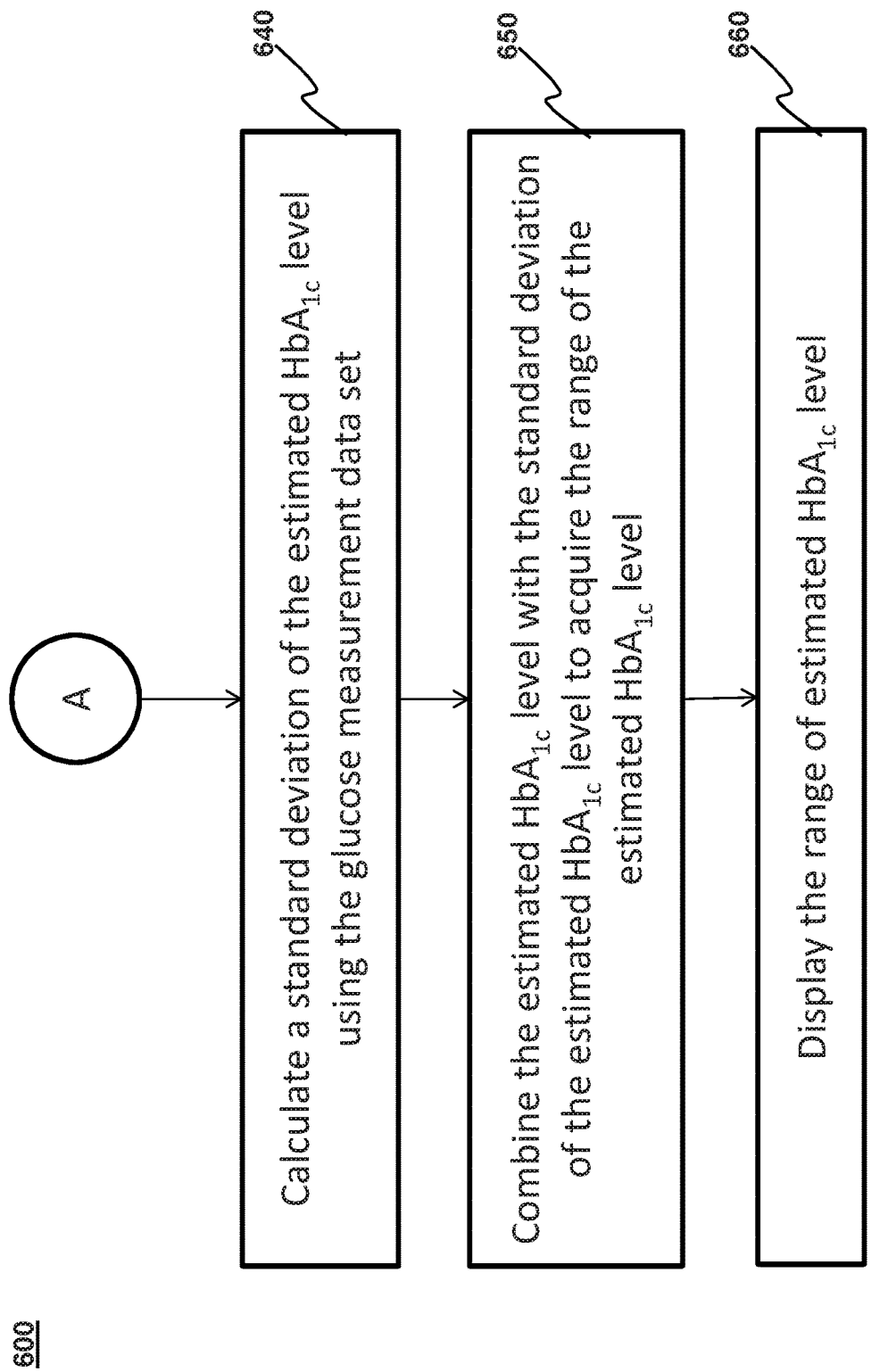
Figure 7:
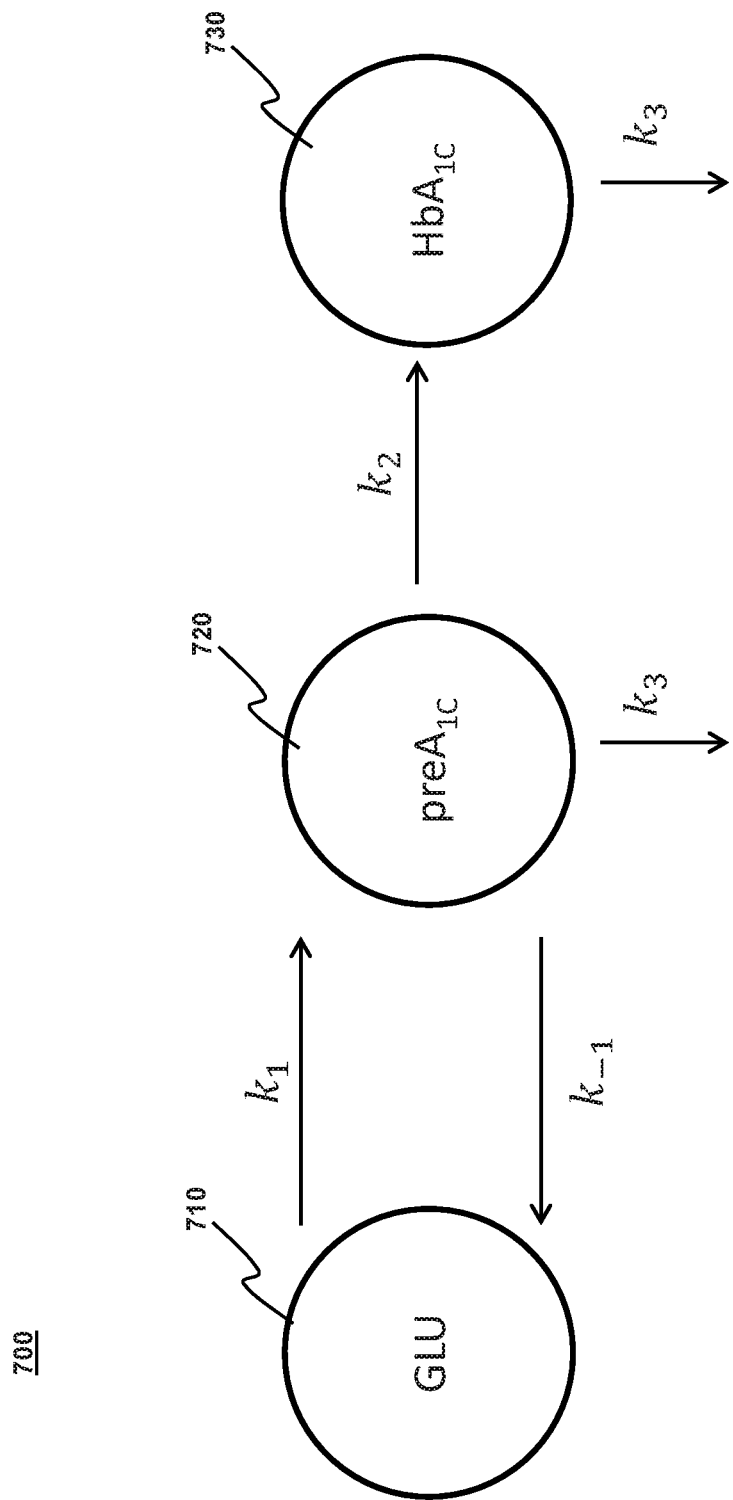
FIG. 7 illustrates an $HbA_{1c}$ kinetic model and embodying aspects of the present invention.

FIGS. 6A-B illustrate a flowchart of an exemplary method 600 of estimating an $HbA_{1c}$ level according to an embodiment of the invention, the method 600 may be based on an $HbA_{1c}$ kinetic model 700. FIG. 7 illustrates a non-limiting example of a kinetic model 700. In some embodiments, as shown in FIG. 7, the $HbA_{1c}$ kinetic model 700 may comprise three states. The First State 710 is when glucose is not yet attached to hemoglobin. The Second State 720 is when the glucose has attached to hemoglobin, but has not fully undergone an arrangement to form the $HbA_{1c}$, referred to as "pre-$A_{1c}$." An association constant $k_1$ represents a binding constant when a glucose attaches to a hemoglobin to form the pre-$A_{1c}$ (moving from the First State 710 to the Second State 720), and an association constant $k_{-1}$ represents a dissociation constant when the glucose detaches from the hemoglobin (moving from the Second State 720 to the First State 710). In a non-limiting embodiment, $k_1 = \sim 7.2 \times 10^{-3}$ mM$^{-1}$ Day$^{-1}$ and $k_{-1} = \sim 7.92$ Day$^{-1}$. However, these specific values are not required, and some alternative embodiments may use different values. The Third State 730 is when the combined glucose and hemoglobin has formed the $HbA_{1c}$. An association constant $k_2$ represents a conversion of the pre-A1c to an $HbA_{1c}$ (moving from the Second State 720 to the Third State 730) and an association constant $k_3$ represents a life span of the pre-A1c and the $HbA_{1c}$. In a non-limiting embodiment, $k_2 = \sim 0.132$ Day$^{-1}$ and $k_3 = \sim 2.45 \times 10^{-2}$ Day$^{-1}$. However, these specific values are not required, and some alternative embodiments may use different values.

Referring back to FIGS. 6A-B, the method 600 of estimating the $HbA_{1c}$ level may be processed by an analyte monitoring device. The analyte monitoring device may be any device in the analyte monitoring system 100, such as the transceiver 120, the primary device 130, and the DMS 140.

In some embodiments, the method 600 may include a step 610, in which the analyte monitoring device obtains one or more glucose measurements of an individual from the analyte monitoring sensor 110. In some embodiments, the analyte monitoring sensor 110 may obtain the one or more glucose measurements by measuring a glucose level of the individual every 1, 2, 5, 10, 15 or 20 minutes. In some embodiments, the frequency in which the analyte monitoring sensor 110 measures glucose levels may be configured based on the individual's preference.

In some embodiments, the method 600 may include a step 620, in which the analyte monitoring device adds the obtained one or more glucose measurements to a glucose measurement data set. In some embodiments, the glucose measurement data set is stored in a memory of the primary device 130 and/or the DMS 140. The glucose measurement data set comprises the measured glucose levels transmitted by the analyte monitoring sensor 110. Accordingly, the amount of information contained in the glucose measurement data set depends on how long the analyte monitoring sensor 110 has been transmitting measured glucose levels of the individual. The accuracy of the estimated $HbA_{1c}$ level range resulting from this method 600 is based on the amount of information contained in the glucose measurement data set. In an embodiment, a user may upload previous glucose level measurements to the glucose measurement data set to enhance the accuracy of the estimated $HbA_{1c}$ level range. For example, if the analyte monitoring sensor 110 is new, glucose measurement data sets acquired from a previous analyte monitoring sensor may be uploaded to the glucose measurement data set to maintain a high level of accuracy for the estimated $HbA_{1c}$ level range.

In some embodiments, the method 600 may include a step 630, in which the analyte monitoring device calculates an estimated $HbA_{1c}$ level using the glucose measurement data set, the association constant $k_2$, and the association constant $k_3$.

In some embodiment, a single exponential approximation equation may be utilized to calculate the estimated $HbA_{1c}$ level. In some embodiments, the single exponential approximation equation may be as follows:

$$\frac{[HbA_{1C}](t)}{[Hb]} \text{(mmol/mol)} \approx \left(1000 \times \frac{[GLU](t)}{[GLU](t) + K_{eq}}\right) * (k_2 e^{-k_3 t}) \quad (5)$$

The single exponential approximation equation (5) is acquired by combining the following equations (6) and (7):

$$\frac{[preA_{1C}]}{[Hb]} \text{(mmol/mol)} \approx 1000 \times \frac{[GLU]}{[GLU] + K_{eq}} \quad (6)$$

$$[HbA_{1C}](t) = [preA_{1C}](t) * k_2 e^{-k_3 t}, \quad (7)$$

wherein, $K_{eq}$ is an association constant that represents an equilibrium constant of glucose and [GLU] represents the glucose measurement data of step 620. In a non-limiting embodiment, $K_{eq}$=110 mM (1982 mg/dL). However, this is not required, and some alternative embodiments may use a different value.

Referring back to equation (5), the estimated $HbA_{1c}$ level may be determined based on a calculation of a convolution of a function of the glucose measurement set and the $K_{eq}$ $$\left(1000 \times \frac{[GLU]}{[GLU] + K_{eq}}\right)$$

with a function of the $k_2$ and $k_3$ association constants ($k_2 e^{-k_3 t}$). Accordingly, the accuracy of the estimated $HbA_{1c}$ level may be based on the amount of information contained in the glucose measurement data set.

In some alternative embodiments, a double exponential approximation equation may be utilized to calculate the estimated $HbA_{1c}$ level. In some embodiments, the double exponential approximation equation may be as follows:

$$\frac{[HbA_{1C}](t)}{[Hb]} \text{(mmol/mol)} = \lceil GLU \rceil(t) * \left(\frac{k_1 k_2}{k_{-1} + k_2}(e^{-k_3 t} - e^{-(k_3 + k_{-1} + k_2)t})\right) \quad (8)$$

As shown above, the estimated $HbA_{1c}$ level may be determined based on a calculation of a convolution the glucose measurement set with a function of the $k_1$, $k_{-1}$, $k_2$, and $k_3$ association constants $$\left(\frac{k_1 k_2}{k_{-1} + k_2}(e^{-k_3 t} - e^{-(k_3 + k_{-1} + k_2)t})\right).$$

Accordingly, the accuracy of the estimated $HbA_{1c}$ level may be based on the amount of information contained in the glucose measurement data set. In some embodiments, the increased complication of the double exponential approximation equation (8) may require higher computational processing requirements for the analyte monitoring device compared to the single exponential approximation equation (6).

In some embodiments, the analyte monitoring device may conduct a calibration procedure for the method 600 of estimating the $HbA_{1c}$ level. In some embodiments, analyte monitoring device may receive calibration data comprising a blood $HbA_{1c}$ measurement of the individual. The analyte monitoring device may compare the estimated $HbA_{1c}$ level with the received blood estimated $HbA_{1c}$ measurement and adjust one or more of the association constant $k_2$, the association constant $k_3$, the association constant $K_{eq}$, the association constant $k_1$, and the association constant $k_{-1}$ values based on the comparison.

In some embodiments, the method 600 may include a step 640, in which the analyte monitoring device calculates a standard deviation of the estimated $HbA_{1c}$ level using the glucose measurement data set.

Another way would be to fit those parameters based for the inverse equation based on a large clinical dataset. A more general method that is not specific to Nathan's work involves simply applying the same model used to estimate HbA1c to the accuracy $$A1C = F(\overline{G(t)}) \begin{array}{l} +F(G(t) + \overline{\Delta}_+ G) \\ -F(G(t) - \overline{\Delta}_- G) \end{array}$$

In some alternative embodiments, the standard deviation of the estimated $HbA_{1c}$ level may be acquired by scaling the standard deviation of the average glucose (equation (2)) by 1/b. In this embodiment, the analyte monitoring device calculates the average glucose (AG) based on the glucose measurement data set and calculates the standard deviation of the estimated $HbA_{1c}$ level using the following equation:

$$\sigma_{(A1C|AG)} = \frac{\sqrt{\left(1 + \frac{1}{n}\right)\beta_1 A1C^{\beta_2}}}{b} \quad (9)$$

In some embodiments, the method 600 may include a step 650, in which the analyte monitoring device combines the estimated $HbA_{1c}$ level from step 630 and the standard deviation of the estimated $HbA_{1c}$ level from step 640 to acquire the range of the estimated $HbA_{1c}$ level.

In some embodiments, the method 600 may include a step 660, in which the analyte monitoring device may cause a connected display to display the range of the estimated $HbA_{1c}$ level. In some embodiments, the range of the estimated $HbA_{1c}$ level may be displayed in a graphical report as shown in FIG. 5. The range of the estimated $HbA_{1c}$ level displayed in the legend 504 along with the curved graph 502 which indicates the amount of time an individual has spent at each of the plurality of glucose ranges. As shown in FIG.

5, the estimated HbA$_{1c}$ level may be indicated along with the range of the estimated HbA$_{1c}$ level to provide the individual an additional indication of the degree of fluctuation of his or her glucose measurements.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

What is claimed is:

1. An analyte monitoring method comprising:
    using an analyte monitoring sensor of an analyte monitoring system to measure glucose levels of a patient, wherein using the analyte monitoring sensor of the analyte monitoring system to measure the glucose levels of the patient comprises using a fluorometer of the analyte monitoring sensor to measure the glucose levels of the patient, using the fluorometer of the analyte monitoring sensor to measure the glucose levels of the patient comprises using the fluorometer to measure parameters of fluorescence after and/or during excitation by a spectrum of light, and the measured parameters include an intensity and/or a wavelength distribution of emission spectrum of the fluorescence;
    using the analyte monitoring sensor to communicate over a wireless communication link;
    using an analyte monitoring device of the analyte monitoring system to obtain a first glucose measurement indicative of a first glucose level of the patient;
    using the analyte monitoring device to obtain a second glucose measurement indicative of a second glucose level of the patient;
    using the analyte monitoring device to add the first and the second glucose measurements to a glucose measurement data set;
    using a processor of the analyte monitoring device to calculate an estimated HbA$_{1c}$ level using the glucose measurement data set, an association constant $k_2$, and an association constant $k_3$, wherein the association constant $k_2$ represents a conversion of a pre-A$_{1c}$ to an HbA$_{1c}$, and the association constant $k_3$ represents a life span of the pre-A$_{1c}$ and the HbA$_{1c}$; and
    using a display of the analyte monitoring device to display the estimated HbA$_{1c}$ level.

2. The method of claim 1, wherein calculating the estimated HbA$_{1c}$ level comprises taking a convolution of a first function and a second function, wherein the first function includes the glucose measurement data set, and the second function includes the association constant $k_2$ and the association constant $k_3$.

3. The method of claim 2, wherein the first function further includes an association constant $K_{eq}$ that represents an equilibrium constant of glucose.

4. The method of claim 2, wherein the second function further includes an association constant $k_1$ and an association constant $k_{-1}$, the association constant $k_1$ represents a binding constant when a glucose attaches to a hemoglobin to form the pre-A$_{1c}$, and the association constant $k_{-1}$ represents a dissociation constant when the glucose detaches from the hemoglobin.

5. The method of claim 1, further comprising:
    using the analyte monitoring device to receive a blood HbA$_{1c}$ measurement; and
    using the analyte monitoring device to calibrate one or more of the first and second functions using the received blood HbA$_{1c}$ measurement.

6. The method of claim 5, wherein calibrating the one or more of the first and second functions comprises:
    adjusting one or more of the association constant $k_2$, the association constant $k_3$, the association constant $K_{eq}$, the association constant $k_1$, and the association constant $k_{-1}$.

7. The method of claim 1, wherein the glucose levels are interstitial fluid glucose levels.

8. The method of claim 1, further comprising employing the measured parameters to identify a presence and/or an amount of specific molecules in a medium.

9. The method of claim 1, wherein the analyte monitoring sensor is an implantable sensor inserted subcutaneously inside the patient.

10. The method of claim 1, wherein the analyte monitoring system obtains the first and second glucose measurements directly from the analyte monitoring sensor.

11. The method of claim 1, wherein the analyte monitoring system obtains the first and second glucose measurements from a transceiver of the analyte monitoring system.

12. The method of claim 1, further comprising using a transceiver of the analyte monitoring system to receive the measured parameters from the analyte monitoring sensor, wherein the analyte monitoring device obtains the first and second glucose measurements from the transceiver.

13. The method of claim 1, further comprising:
    using the processor of the analyte monitoring device to calculate a standard deviation of the estimated HbA$_{1c}$ level using the glucose measurement data set;
    using the processor of the analyte monitoring device to combine the estimated HbA$_{1c}$ level with the standard deviation of the estimated HbA$_{1c}$ level to acquire a range of the estimated HbA$_{1c}$ level; and
    using a display of the analyte monitoring device to display the range of the estimated HbA$_{1c}$ level.

14. The method of claim 1, wherein the processor of the analyte monitoring device uses the following formula to calculate the estimated HbA$_{1c}$ level:

$$\frac{[HbA_{1c}]}{[Hb]}\left(\frac{\text{mmol}}{\text{mol}}\right) = [GLU](t) * \left(\frac{k_1 k_2}{k_{-1}+k_2}\left(e^{-k_3 t} - e^{-(k_3+k_{-1}+k_2)t}\right)\right),$$

where $k_1$ is an association constant that represents a binding constant when a glucose attaches to a hemoglobin to form the pre-A$_{1c}$, and $k_{-1}$ is an association constant that represents a dissociation constant when the glucose detaches from the hemoglobin.

15. An analyte monitoring method comprising:
    using an analyte monitoring sensor of an analyte monitoring system to measure glucose levels of a patient, wherein using the analyte monitoring sensor of the analyte monitoring system to measure the glucose levels of the patient comprises using a fluorometer of the analyte monitoring sensor to measure the glucose levels of the patient, using the fluorometer of the analyte monitoring sensor to measure the glucose levels of the patient comprises using the fluorometer to measure parameters of fluorescence after and/or during excitation by a spectrum of light, and the measured parameters include an intensity and/or a wavelength distribution of emission spectrum of the fluorescence;

using the analyte monitoring sensor to communicate over a wireless communication link;

using an analyte monitoring device of the analyte monitoring system to obtain a first glucose measurement indicative of a first glucose level of the patient;

using the analyte monitoring device to obtain a second glucose measurement indicative of a second glucose level of the patient;

using the analyte monitoring device to add the first and the second glucose measurements to a glucose measurement data set;

using a processor of the analyte monitoring device to calculate an estimated $HbA_{1c}$ level using the glucose measurement data set and the following formula:

$$\frac{[HbA_{1c}]}{[Hb]}\left(\frac{\text{mmol}}{\text{mol}}\right) = [GLU](t) * \left(\frac{k_1 k_2}{k_{-1} + k_2}\left(e^{-k_3 t} - e^{-(k_3 + k_{-1} + k_2)t}\right)\right)$$

where $k_1$ is an association constant that represents a binding constant when a glucose attaches to a hemoglobin to form a pre-$A_{1c}$, $k_{-1}$ is an association constant that represents a dissociation constant when the glucose detaches from the hemoglobin, $k_2$ is an association constant that represents a conversion of the pre-$A_{1c}$ to an $HbA_{1c}$ and $k_3$ is an association constant that represents a life span of the pre-$A_{1c}$ and the $HbA_{1c}$;

using the processor of the analyte monitoring device to calculate a standard deviation of the estimated $HbA_{1c}$ level using the glucose measurement data set;

using the processor of the analyte monitoring device to combine the estimated $HbA_{1c}$ level with the standard deviation of the estimated $HbA_{1c}$ level to acquire a range of the estimated $HbA_{1c}$ level; and using a display of the analyte monitoring device to display the range of the estimated $HbA_{1c}$ level.

16. The method of claim 15, wherein the glucose levels are interstitial fluid glucose levels.

17. The method of claim 15, further comprising employing the measured parameters to identify a presence and/or an amount of specific molecules in a medium.

18. The method of claim 15, wherein the analyte monitoring sensor is an implantable sensor inserted subcutaneously inside the patient.

19. The method of claim 15, wherein the analyte monitoring system obtains the first and second glucose measurements directly from the analyte monitoring sensor.

20. The method of claim 15, wherein the analyte monitoring system obtains the first and second glucose measurements from a transceiver of the analyte monitoring system.

21. The method of claim 15, further comprising using a transceiver of the analyte monitoring system to receive the measured parameters from the analyte monitoring sensor, wherein the analyte monitoring device obtains the first and second glucose measurements from the transceiver.

* * * * *